US011446220B2

(12) United States Patent
Wang et al.

(10) Patent No.: US 11,446,220 B2
(45) Date of Patent: Sep. 20, 2022

(54) TRANSPARENT HAIR LIGHTENING COMPOSITIONS, KITS, AND METHODS OF USE

(71) Applicant: L'OREAL, Paris (FR)

(72) Inventors: Jeffrey Wang, Clark, NJ (US); Jeremy Puco, West Caldwell, NJ (US)

(73) Assignee: L'OREAL, Paris (FR)

(*) Notice: Subject to any disclaimer, the term of this patent is extended or adjusted under 35 U.S.C. 154(b) by 1052 days.

(21) Appl. No.: 15/639,530

(22) Filed: Jun. 30, 2017

(65) Prior Publication Data
US 2019/0000732 A1 Jan. 3, 2019

(51) Int. Cl.
A61Q 5/08 (2006.01)
A61K 8/23 (2006.01)
A61K 8/22 (2006.01)
A61K 8/73 (2006.01)
A61K 8/81 (2006.01)
A61K 8/87 (2006.01)

(52) U.S. Cl.
CPC .............. A61K 8/23 (2013.01); A61K 8/22 (2013.01); A61K 8/73 (2013.01); A61K 8/737 (2013.01); A61K 8/8147 (2013.01); A61K 8/8152 (2013.01); A61K 8/87 (2013.01); A61Q 5/08 (2013.01); A61K 2800/262 (2013.01)

(58) Field of Classification Search
None
See application file for complete search history.

(56) References Cited

U.S. PATENT DOCUMENTS

| 7,601,179 | B2 | 10/2009 | Allard et al. |
|---|---|---|---|
| 7,611,544 | B2 | 11/2009 | Allard et al. |
| 7,905,926 | B2 | 3/2011 | Degeorge et al. |
| 7,981,403 | B2 | 7/2011 | Cannell et al. |
| 8,088,176 | B2 | 1/2012 | Degeorge et al. |
| 8,163,037 | B2 | 4/2012 | Degeorge et al. |
| 8,343,238 | B1 | 1/2013 | Lopez et al. |
| 8,506,651 | B2 | 8/2013 | Lopez et al. |
| 8,556,992 | B2 | 10/2013 | Degeorge et al. |
| 8,556,994 | B2 | 10/2013 | Lopez et al. |
| 9,265,717 | B1 | 2/2016 | Degeorge et al. |
| 9,295,632 | B1 | 3/2016 | Benn et al. |
| 9,474,700 | B2 | 10/2016 | Salvemini et al. |
| 9,565,915 | B2 | 2/2017 | Degeorge et al. |
| 9,565,916 | B2 | 2/2017 | Degeorge et al. |
| 9,566,221 | B2 | 2/2017 | Degeorge et al. |
| 2006/0269492 | A1* | 11/2006 | Narasimhan .............. A61K 8/23 424/62 |
| 2010/0247470 | A1* | 9/2010 | Friel ........................ A61K 8/39 424/70.7 |
| 2011/0104090 | A1* | 5/2011 | Kelton ..................... A61Q 5/12 424/62 |
| 2013/0042883 | A1* | 2/2013 | DeGeorge ................ A61K 8/23 132/208 |
| 2016/0058687 | A1* | 3/2016 | Anderheggen ...... A61K 8/8147 132/208 |
| 2016/0303014 | A1* | 10/2016 | Grevalcuore .......... A61K 8/447 |

* cited by examiner

Primary Examiner — Jyothsna A Venkat
(74) Attorney, Agent, or Firm — Polsinelli PC

(57) ABSTRACT

The present disclosure relates to transparent ready-to-use hair bleaching compositions and compositions useful for preparing the transparent ready-to-use hair bleaching compositions. The transparent ready-to-use bleaching compositions typically include: (i) one or more oxidizing agents selected from the group consisting of persulfates, perborates, percarbonates, a salt thereof, and a mixture thereof; (ii) one or more non-acrylic thickening polymers; (iii) one or more acrylic polymers; (iv) hydrogen peroxide; (v) one or more polyurethane polyethers; and (vi) water. Kits and methods for bleaching hair also disclosed.

11 Claims, No Drawings

TRANSPARENT HAIR LIGHTENING COMPOSITIONS, KITS, AND METHODS OF USE

FIELD OF THE DISCLOSURE

The present disclosure relates to transparent ready-to-use hair bleaching compositions, kits comprising bleach compositions and developer compositions, and methods for treating hair.

BACKGROUND

Consumers use cosmetic and care compositions that enhance the appearance of hair, e.g., by changing the color, style, and/or shape of the hair, and/or by imparting various properties to hair, such as shine and conditioning. Many of the known compositions and processes for enhancing the appearance of the hair involve chemical treatment of the hair. The process of changing the color of hair, for example, can involve depositing an artificial color onto the hair which provides a different shade or color to the hair, and/or lifting the color of the hair (bleaching), such as lightening the color of dark hair to lighter shades. The process of lifting the color of hair, also known as lightening, generally requires the use of compositions that comprise at least one oxidizing agent.

Bleaching or lifting the color of the hair is typically evaluated by the variation in tone height before and after the application of a hair color-altering composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels range from 1 (black) to 10 (light blond), one unit corresponding to one tone; thus, the higher the number, the lighter the shade or the greater the degree of lift.

In general, hair lightening or color lifting compositions and hair dyeing compositions possess an alkalinity such that these compositions have a pH value of above 7, typically being at pH 9 and above, and may generally require the presence of an alkalizing agent such as ammonia or an ammonia gas generating compound and/or an amine or ammonium-based compound in amounts sufficient to make such compositions alkaline. The alkalizing agent causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

SUMMARY OF THE DISCLOSURE

The compositions of the instant disclosure are useful for bleaching hair and are unique in that they themselves are transparent or are combined with other components or compositions to provide a transparent ready-to-use bleaching composition. Transparent ready-to-use bleaching compositions are particularly useful because they allow for one to visualize the bleaching process while it occurs, i.e., the allow one to see the degree to which hair being bleached changes color (lightens) during the bleaching process. Typical bleaching compositions are opaque. Therefore, determining whether sufficient bleaching (or lightening) of the hair has occurred requires physically removing at least a portion of the opaque composition from the hair. To visualize the color change of an entire head of hair requires removing (typically rinsing) the opaque bleaching composition from the entire head of hair. If the hair has not reached the desired lightness or color at the time of rinsing, additional bleaching composition must then be applied to the hair and further bleaching of the hair carried out.

The transparent ready-to-use bleaching compositions may be formed by combining a bleach composition of the instant disclosure with a developer composition. Bleach compositions and developer compositions are typically stored or packaged separately and combined shortly before use. Bleach compositions of the instant disclosure typically include:
  i. one or more oxidizing agents selected from the group consisting of persulfates, perborates, percarbonates, a salt thereof, and a mixture thereof;
  ii. one or more non-acrylic thickening polymers; and
  iii. one or more acrylic polymers.

The bleach compositions may optionally be anhydrous or essentially anhydrous and may additionally include, for example, ammonium salt(s), alkaline agent(s), oil(s), silicate(s), silica, chelating agent(s), fragrance(s), etc.

Developer compositions of the instant disclosure typically include:
  i. hydrogen peroxide;
  ii. one or more polyurethane polyethers; and
  ii. water.

The developer compositions may additionally include components such as surfactant(s), preservative(s), fragrance(s), etc.

The amount of developer composition needed to be combined with a bleach composition can vary depending on the amount (or strength) of the hydrogen peroxide in the developer composition. Also, the amount of developer composition to be combined with the bleach composition can vary depending on the desired strength of the resulting transparent ready-to-use bleaching composition, which is often determined by the degree of lightening desired, the original color of the hair to be bleached, the type (or ethnicity) of hair to be bleached, etc.

Although transparent ready-to-use bleaching compositions can be prepared by combining bleach compositions and developer compositions, as outlined above, it is not necessary to prepare the transparent ready-to-use bleaching compositions of the instant disclosure using the specific bleach compositions and developer compositions described herein. In other words, each component of the transparent ready-to-use compositions can come from either, both, or neither of the bleach compositions and/or the developer compositions of the instant disclosure. It is irrelevant whether each component of the transparent ready-to-use bleaching composition was previously part of a bleach composition, a developer composition, or a completely independent composition (or not part of any prior composition).

Transparent ready-to-use hair bleaching compositions typically include:
  i. one or more oxidizing agents selected from the group consisting of persulfates, perborates, percarbonates, a salt thereof, and a mixture thereof;
  ii. one or more non-acrylic thickening polymers;
  iii. one or more acrylic polymers;
  iv. hydrogen peroxide;
  v. one or more polyurethane polyethers; and
  vi. water.

Non-limiting examples of non-acrylic thickening agents that are useful in the instant compositions include xanthan gum, cellulose gum, guar gum, algin, chitosan, hydroxyethylcellulose, hydroxypropylcellulose, cetyl hydroxyethylcellulose, polyvinylpyrrolidone, and a mixture thereof. In some cases, xanthan gum is particularly useful.

Non-limiting examples of acrylic polymers that are useful in the compositions of the instant disclosure include crosslinked acrylic polymers. Non-limiting examples of crosslinked acrylic polymer include sodium polyacrylate, carbomer, acrylates C10-30 alkyl acrylate crosspolymer, or a mixture thereof.

Useful polyurethane polyethers include polyoxyethylenated polyurethane polyether. A non-limiting example of a olyoxyethylenated polyurethane polyether includes disteareth-100 IPDI.

The transparent ready-to-use bleaching compositions may include one or more alkaline agents, such as alkali metal phosphates and carbonates. Furthermore, components such as fatty compounds (including oils), preservatives, cationic conditioning compounds (including cationic conditioning polymers), chelating agents, fragrances, amino acids, surfactants (cationic, anionic, nonionic, and/or amphoteric), etc., may be included or excluded from the transparent ready-to-use bleaching compositions.

The instant disclosure also relates to kits, which typically include a bleach composition and a developer composition, wherein the bleach composition and the developer composition are separately packaged or contained. When the bleach composition and developer composition are combined, a transparent ready-to-use composition is formed. Instructions, mixing components, brushes, gloves, measuring tools, etc., may also be included in the kits.

The various compositions of the disclosure and the kits are useful in methods for bleaching hair (or lightening hair or coloring hair). The methods typically include applying a transparent ready-to-use bleaching composition to hair; allowing the composition to remain on the hair for a period of time; and rinsing the composition from the hair. The methods may further include obtaining a bleach composition and a developer composition of the instant disclosure, and combining the compositions to derive a transparent ready-to-use bleaching composition, which can then be used in methods for bleaching hair (or lightening hair or coloring hair).

DETAILED DESCRIPTION OF THE DISCLOSURE

The instant disclosure relates to compositions that are useful for bleaching, lightening, and/or coloring hair. Typically, a bleach composition and a developer composition are combined to form a unique, transparent ready-to-use bleaching composition. The terms "bleach composition," "developer composition," and "bleaching composition" are used throughout the disclosure. A "bleach composition" is different than a "bleaching composition." A "bleach composition" comprises one or more oxidizing agents and is combined with a "developer composition" to form a "bleaching composition." Thus, a "bleach composition" is a component of a "bleaching composition." A "developer composition" is a composition for combination with the bleach composition; it typically includes at least hydrogen peroxide and water. The bleaching compositions of the instant disclosure are transparent and are typically referred to as "ready-to-use" compositions because these compositions are ready to be applied to hair.

The term "transparent" with respect to compositions of the instant disclosure indicates that the composition has transmittance of at least 80% at a wavelength of 600 nm, for example measured using a Lambda 40 UV-visible spectrometer, at a concentration of 0.5% by weight in water. The compositions may have, for example, a transmittance of at least 80%, at least 90%, or at least 95% at a wavelength of 600 nm, measured, for example, using a Lambda 40 UV-visible spectrometer. Additionally, a "transparent" composition according to the disclosure may have a refractory index of about 1.3 to about 1.4 at 25° C. For reference, pure water has a refractive index of 1.33 at 25° C. The transparent bleaching compositions of the instant disclosure generally have a refractive index of about 1.33 to about 1.37, about 1.33 to about 1.36, about 1.34 to about 1.37, or about 1.34 to about 1.36.

Bleach compositions of the disclosure typically include one or more oxidizing agents selected from the group consisting of persulfates, perborates, percarbonates, a salt thereof, and a mixture thereof. In some instances, the bleach compositions are anhydrous or essentially anhydrous. More specifically, bleach compositions typically include:

i. one or more oxidizing agents selected from the group consisting of persulfates, perborates, percarbonates, a salt thereof, and a mixture thereof;

ii. one or more non-acrylic thickening polymers; and iii. one or more acrylic polymers.

The one or more oxidizing agents referenced above are selected from the group consisting of persulfates, perborates, percarbonates, a salt thereof, and a mixture thereof. In some instances, however, the bleach compositions can include, as oxidizing agents, one or more of alkali metal bromates, ferricyanides, redox enzymes such as laccases, peroxidases, and 2-electron oxidoreductases, such as uricase. These oxidizing agents may be used in place of the one or more oxidizing agents selected from the group consisting of persulfates, perborates, percarbonates, a salt thereof, and a mixture thereof, or these oxidizing agents may be combined with the one or more oxidizing agents selected from the group consisting of persulfates, perborates, percarbonates, a salt thereof, and a mixture thereof.

The developer compositions of the disclosure are typically aqueous compositions comprising hydrogen peroxide. For instance, the developer compositions may include:

i. hydrogen peroxide;

ii. one or more polyurethane polyethers; and ii. water.

The ready-to-use bleaching compositions of the disclosure typically contain the components of both the bleach compositions and the developer compositions. The amount of developer composition needed to be combined with the bleach composition can vary depending on the amount (or strength) of the hydrogen peroxide in the developer composition. Also, the amount of developer composition to be combined with the bleach composition can vary depending on the desired strength of the resulting ready-to-use bleaching composition, which is often determined by the degree of lightening desired, the original color of the hair to be treated, the type of hair to be treated, etc. In some instances, an amount of bleach composition is combined with an amount of developer composition in a ratio of about 1:5 to about 5:1. The ratio of bleach composition to developer composition may also be about 1:4 to about 4:1, about 1:3 to about 3:1, about 1:2 to about 2:1, or about 1:1.

The total amount of oxidizing agents in the bleach composition may vary but is typically about 25 to about 85 wt. %, based on the total weight of the bleach compositions. In some cases, the total amount of the oxidizing agents is about 30 to about 85 wt. %, about 30 to about 85 wt. %, about 40 to about 85 wt. %, about 45 to about 85 wt. %, about 50 to about 85 wt. %, about 25 to about 80 wt. %, about 30 to about 80 wt. %, about 35 to about 80 wt. %, about 40 to about 80 wt. %, or about 50 to about 75 wt. %, based on the total weight of the bleach composition.

Non-limiting examples of non-acrylic thickening agents include carboxylic acid/carboxylate copolymers, hydrophobically-modified cross-linked copolymers of carboxylic acid and alkyl carboxylate vinyl polymers, methyl cellulose, ethyl cellulose, hydroxyethyl cellulose, hydroxylpropyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, polyethyleneimine, bentonite, aluminum magnesium silicate, laponite, hectonite, anhydrous silicic acid, and a mixture thereof.

In some cases, the one or more thickening agents are selected from the group consisting of methyl cellulose, ethyl cellulose, hydroxyethyl cellulose, hydroxypropyl methyl cellulose, hydroxylpropyl cellulose, sodium carboxymethyl cellulose, polyvinylpyrrolidone, polyvinyl alcohol, guar gum, hydroxypropyl guar gum, xanthan gum, arabic gum, carrageenan, starch-based polymers, and a mixture thereof. Furthermore, in some cases, non-acrylic thickening agents that are useful in the instant compositions include xanthan gum, cellulose gum, guar gum, algin, chitosan, hydroxyethylcellulose, hydroxypropylcellulose, cetyl hydroxyethylcellulose, polyvinylpyrrolidone, and a mixture thereof. In some cases, xanthan gum is particularly useful. In some cases, it may be preferable to exclude cellulose thickeners, such as cellulose gum, etc.

The total amount of the one or more non-acrylic thickening agents may vary but is typically about 0.1 to about 15 wt. %, based on the total weight of the hair bleach composition. In some cases, the total amount of non-acrylic thickening agents may be about 0.1 to about 12 wt. %, about 0.1 to about 10 wt. %, about 0.1 to about 8 wt. %, about 0.1 to about 6 wt. %, about 0.1 to about 5 wt. %, about 0.5 to about 15 wt. %, about 0.5 to about 12 wt. %, about 0.5 to about 10 wt. %, about 0.5 to about 8 wt. %, about 0.5 to about 6 wt. %, about 0.5 to about 5 wt. %, about 1 to about 12 wt. %, about 1 to about 10 wt. %, about 1 to about 8 wt. %, about to about 6 wt. %, or about 1 to about 5 wt. %, based on the total weight of the bleach composition.

Non-limiting examples of acrylic polymers that are useful in the bleach compositions include crosslinked acrylic polymers. Non-limiting examples of crosslinked acrylic polymer include sodium polyacrylate, carbomer, acrylates C10-30 alkyl acrylate crosspolymer, or a mixture thereof. In some instances, the one or more acrylic polymers are crosslinked acrylic polymers. Crosslinked acrylic polymers can be selected from modified or unmodified carboxyvinyl polymers, such as copolymers of acrylic acid and of C10-C30 alkyl acrylate or methacrylate, for instance the products sold under the tradenames CARBOPOL and PEMULEN (INCI names: carbomer, acrylates/C10-30 alkyl acrylate crosspolymer) by the company Lubrizol, or such as the crosslinked sodium polyacrylate sold under the name COSMEDIA SP by the company Cognis (BASF) (INCI name: sodium polyacrylate). Among the crosslinked acrylic polymers, sodium polyacrylate, carbomer, and acrylates/C10-30 alkyl acrylate crosspolymer are useful. Also, the crosslinked acrylic polymer, sodium polyacrylate and/or acrylates/C10-30 alkyl acrylate crosspolymer are particularly useful.

The total amount of the one or more acrylic polymers may vary but is typically about 0.1 to about 20 wt. %, based on the total weight of the bleach composition. In some cases, the total amount of the one or more acrylic polymers is about 0.1 to about 15 wt. %, about 0.1 to about 10 wt. %, about 0.1 to about 5 wt. %, about 1 to about 20 wt. %, about 1 to about 15 wt. %, about 1 to about 10 wt. %, about 1 to about 8 wt. %, or about 1 to about 6 wt. %, based on the total weight of the bleach composition.

The bleach composition may optionally include one or more ammonium salts. Non-limiting examples of ammonium salts include ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate, ammonium lactate, and a mixture thereof.

The total amount of the one or more ammonium salts may vary but is typically about 0.1 to about 10 wt. %, based on the total weight of the bleach composition. In some cases, the total amount of the one or more ammonium salts is about 0.1 to about 8 wt. %, about 0.1 to about 6 wt. %, about 0.1 to about 4 wt. %, about 0.5 to about 10 wt. %, about 0.5 to about 8 wt. %, about 0.5 to about 6 wt. %, about 0.5 to about 4 wt. or about 0.5 to about 3 wt. %, based on the total weight of the bleach composition.

Additionally, the bleach composition may include one or more alkaline agents other than the one or more ammonium salts (discussed above). Non-limiting examples include carbonates such as potassium carbonate and sodium hydrogencarbonate, alkanolamines, organic amines, a basic amino acid, and salts thereof. Non-limiting examples of an alkanolamine include monoethanolamine and triethanolamine. Non-limiting examples of an organic amine include 2-amino-2-methyl-1-propanol (AMP), 2-amino-2-methyl-1,3-propanediol, and guanidine. Non-limiting examples of basic amino acids include arginine and lysine. In some cases, carbonates, such as potassium carbonate are particularly useful.

The total amount of the one or more alkaline agents other than the one or more ammonium salts may vary but is typically about 0.1 to about 15 wt. %, based on the total weight of the bleach composition. In some cases, the total amount of the one or more alkaline agents other than the one or more ammoniums salts is about 0.1 to about 12 wt. %, about 0.1 to about 10 wt. %, about 0.1 to about 8 wt. %, about 0.1. to about 6 wt. %, about 0.1 to about 5 wt. %, about 1 to about 15 wt. %, about 1 to about 12 wt. %, about 1 to about 12 wt. %, about 1 to about 10 wt. %, about 1 to about 8 wt. %, about 1 to about 6 wt. %, or about 1 to about 5 wt. %, based on the total weight of the bleach composition.

In some instances, the bleach composition includes one or more oils. The one or more oils typically include those generally used in cosmetics and particularly from oils of animal, vegetable or mineral origin, linear or branched hydrocarbons, optionally branched and/or unsaturated fatty acids, optionally branched and/or unsaturated fatty alcohols, mono- and/or polyesters of fatty acids and/or of fatty alcohols, perfluorinated and/or orgaofluorinated oils, volatile or non-volatile silicone oils, fluorosilicone oils and their mixtures. Mention is made, as an example of linear or branched hydrocarbons, of oils of mineral or synthetic origin, such as liquid paraffins and their derivatives, petrolatum, mineral oils, (mixtures of oil-derived hydrocarbon oils), polybutene, hydrogenated polyisobutene, polyisoprene, polydecenes such as hydrogenated polydecene, or also linear, branched and/or cyclic alkanes which are optionally volatile, such as, for example, isohexadecane, isododecane, isodecane or isohexadecane, and their mixtures.

The total amount of the one or more oils in the bleach composition may vary but is typically about 0.1 to about 10 wt. %, based on the total weight of the bleach composition. In some cases, the total amount of the one or more oils may be about 0.1 to about 8 wt. %, about 0.1 to about 6 wt. %, about 0.1 to about 4 wt. %, or about 0.1 to about 2 wt. %, based on the total weight of the bleach composition.

The bleach compositions may also include one or more silicates. Non-limiting examples of silicates include lithium, sodium, and potassium silicates, metasilicates and disilicates, and a combination thereof, including mixed lithium, sodium, and potassium salts thereof. Specific non-limiting examples include aluminum silicate, magnesium silicate, aluminum magnesium silicate, calcium silicate, barium silicate, strontium silicate, and a mixture thereof.

The total amount of the one or more silicates in the bleach composition may vary but is typically about 1 to about 60 wt. % based on the total weight of the bleach composition. In some cases, the total amount of the one or more silicates is about 1 to about 50 wt. %, about 5 to about 60 wt. %, about 5 to about 50 wt. %, about 10 to about 60 wt. %, about 10 to about 50 wt. %, about 15 to about 60 wt. %, about 15 to about 50 wt. %, about 20 to about 60 wt. %, about 20 to about 50 wt. %, about 30 to about 60 wt. %, or about 30 to about 50 wt. %, based on the total weight of the bleach composition.

The bleach compositions of the instant disclosure may be provided in a variety of different forms. For example, the bleach composition may be a solid, a powder, a gel, a paste, a lotion, a cream, etc. In some cases, the bleach composition is largely free of water. In other words, the bleach composition is anhydrous or essentially anhydrous. For example, the bleach composition includes less than 5 wt. % water, based on the total weight of the bleach composition. Additionally, the bleach composition may include less than 4 wt. %, less than 3 wt. %, less than 2 wt. %, less than 1 wt. %, or less than 0.5 wt. % water, based on the total weight of the bleach composition. In some cases, the bleach composition is a powder composition that contains less than 1 wt. % of water.

Additional components may also be included in the bleach compositions such as, for example, preservatives, cationic conditioning compounds including cationic conditioning polymers, chelating agents, fragrances, amino acids, surfactants (cationic, anionic, nonionic, and/or amphoteric), etc.

The developer compositions of the instant disclosure are typically aqueous compositions comprising (i) hydrogen peroxide; (ii) one or more polyurethane polyethers; and (iii) water. The total amount of hydrogen peroxide and water in the developer composition can vary greatly depending on the desired strength of the developer compositions. In some case, the total amount of hydrogen peroxide in the developer composition is about 1 to about 40 wt. %, based on the total weight of the developer composition. For instance, the total amount of the hydrogen peroxide may be about 1 to about 35 wt. %, about 1 to about 30 wt. %, about 1 to about 25 wt. %, about 1 to about 20 wt. %, about 1 to about 15 wt. %, about 1 to about 10 wt. %, about 2 to about 40 wt. %, about 2 to about 35 wt. %, about 2 to about 30 wt. %, about 2 to about 25 wt. %, about 2 to about 20 wt. %, about 2 to about 15 wt. %, or about 2 to about 10 wt. %, based on the total weight of the developer composition.

Particularly useful polyurethane polyethers that may be included in the developer compositions include polyoxyethylenated polyurethane polyethers. A non-limiting example of a polyoxyethylenated polyurethane polyether includes disteareth-100 IPDI. Also useful are polyurethane polyethers comprising in their chain both hydrophilic blocks usually of polyoxyethylenated nature and hydrophobic blocks, which may be aliphatic sequences alone and/or cycloaliphatic and/or aromatic sequences (e.g., nonionic fatty-chain polyurethane polyethers). In some instances, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. Furthermore, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

Nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane linkage between the hydrophilic blocks, whence arises the name. By extension, also included among the nonionic fatty-chain polyurethane polyethers are those in which the hydrophilic blocks are linked to the lipophilic blocks via other chemical bonds. As examples of nonionic fatty-chain polyurethane polyethers that may be used in the invention, it is also possible to use RHEOLATE 205 containing a urea function, sold by the company Rheox, or RHEOLAT. 208, 204 or 212, and also ACRYSOL 84. Mention may also be made of the product ELFACOS T210 containing a $C_{12-14}$ alkyl chain, and the product ELFACOS T212 containing a $C_{18}$ alkyl chain, from Akzo.

The product DW 1206B from Rohm & Haas containing a $C_{20}$ alkyl chain and a urethane linkage, sold at a solids content of 20% in water, may also be used. It is also possible to use solutions or dispersions of these polymers, especially in water or in aqueous-alcoholic medium. Examples of such polymers that may be mentioned are RHEOLATE 255, RHEOLATE 278 and RHEOLATE 244 sold by the company Rheox. The products DW 1206F and DW 1206J sold by the company Rohm & Haas may also be used.

The polyurethane polyethers that may be used include those described in the article by G. Fonnum, J. Bakke and Fk. Hansen—Colloid Polym. Sci 271, 380.389 (1993).

In some cases, it may be useful to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate. Such polyurethane polyethers are sold especially by the company Rohm & Haas under the names ACULYN 46 and ACULYN 44. ACULYN 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%). ACULYN 44 is a polycondensate of polyethylene glycol containing 150 or 180 mol of ethylene oxide, of decyl alcohol and of methylenebis(4-cyclohexyl-isocyanate) (SMDI), at 35% by weight in a mixture of propylene glycol (39%) and water (26%).

The total amount of the one or more polyurethane polyethers may vary but is typically about 0.1 to about 30 wt. %, based on the total weight of the developer composition. In some cases, the total amount of the one or more polyurethane polyethers is about 0.1 to about 25 wt. %, about 0.1 to about 20 wt. %, about 0.1 to about 15 wt. %, about 0.1 to about 10 wt. %, about 0.5 to about 25 wt. %, about 0.5 to about 20 wt. %, about 0.5 to about 15 wt. %, about 0.5 to about 10 wt. %, about 1 to about 25 wt. %, about 1 to about 20 wt. %, about 1 to about 15 wt. %, about 1 to about 10 wt. %, or about 1 to about 8 wt. %, based on the total weight of the developer composition.

In some cases, the developer composition may include one or more surfactants such as one or more nonionic, anionic, cationic, or amphoteric surfactants. In some cases, however, the one or more surfactants include at least one nonionic surfactant. Non-limiting examples of nonionic surfactants include polyoxyalkylenated or polyglycerolated nonionic surfactants. The oxyalkylene units are more particularly oxyethylene or oxypropylene units, or a combination thereof, and are preferably oxyethylene units. Non-limiting examples of oxyalkylenated nonionic surfactants that may be mentioned include: oxyalkylenated ($C_8$-$C_{24}$) alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

A more exhaustive list of anionic surfactants that may be included in the hair-treatment compositions is provided later, under the heading "Nonionic Surfactants."

The total amount of the one or more nonionic surfactants may vary but it typically about 0.01 to about 10 wt. %, based on the total amount of the developer composition. In some cases, the total amount of nonionic surfactant is about 0.01 to about 8 wt. %, about 0.01 to about 6 wt. %, about 0.01 to about 4 wt. %, about 0.01 to about 2 wt. %, about 0.05 to about 8 wt. %, about 0.05 to about 6 wt. %, about 0.05 to about 4 wt. %, or about 0.05 to about 2 wt. %, based on the total weight of the developer composition.

As noted above, the developer composition is typically an aqueous composition and therefore includes water. The total amount of water may vary but in some cases is about 40 to about 96 wt. %, based on the total weight of the developer composition. In some cases, the total amount of water is about 50 to about 96 wt. %, about 60 to about 96 wt. %, about 70 to about 96 wt. %, about 80 to about 96 wt. %, about 50 to about 95 wt. %, about 60 to about 95 wt. %, about 70 to about 95 wt. %, or about 80 to about 95 wt. %.

The transparent ready-to-use bleaching compositions of the disclosure may be formed by combining bleach compositions and developer compositions discussed above, or may be formed independent of the bleach compositions and developer compositions discussed above. In other words, each component of a transparent ready-to-use composition according to the instant disclosure can come from either, both, or neither of the bleach compositions and/or the developer compositions of the instant disclosure. The transparent ready-to-use hair bleaching compositions of the disclosure include:
i. one or more oxidizing agents selected from the group consisting of persulfates, perborates, percarbonates, a salt thereof, and a mixture thereof;
ii. one or more non-acrylic thickening polymers;
iii. one or more acrylic polymers;
iv. hydrogen peroxide;
v. one or more polyurethane polyethers; and
vi. water.

As noted above, it is irrelevant whether each component of a transparent ready-to-use bleaching composition was previously part of a bleach composition, a developer composition, or a completely independent composition (or not part of any prior composition). However, in some cases, the transparent ready-to-use bleaching compositions of the disclosure can be prepared by combining a bleach composition and a developer composition of the instant disclosure. Accordingly, transparent ready-to-use bleaching compositions may include a combination of:
(a) a bleach composition comprising:
i. one or more oxidizing agents, for example, one or more oxidizing agents selected from the group consisting of persulfates, perborates, percarbonates, a salt thereof, and a mixture thereof;
ii. one or more non-acrylic thickening polymers; and
iii. one or more acrylic polymers; and
(b) a developer composition comprising:
i. hydrogen peroxide;
ii. one or more polyurethane polyethers; and
ii. water.

The amount of developer composition needed to be combined with the bleach composition can vary depending on the amount (or strength) of the hydrogen peroxide in the developer composition. Also, the amount of developer composition to be combined with the bleach composition can vary depending on the desired strength of the resulting ready-to-use bleaching composition, which is often determined by the degree of lightening desired, the original color of the hair to be treated, the type of hair to be treated, etc. In some instances, an amount of bleach composition is combined with an amount of developer composition in a ratio of about 1:5 to about 5:1. The ratio of bleach composition to developer composition may also be about 1:4 to about 4:1, about 1:3 to about 3:1, about 1:2 to about 2:1, or about 1:1.

The amounts provided for the individual bleach compositions and the individual developer compositions discussed above are based on the total weight of the individual compositions. When these compositions are combined, the total weight of each component in the combination may be referred to according to the total weight of the transparent ready-to-use composition (i.e., the total weight of the combination of the bleach compositions and the developer composition).

The one or more oxidizing agents in the transparent ready-to-use bleaching compositions may be selected from the group consisting of persulfates, perborates, percarbonates, a salt thereof, and a mixture thereof. Non-limiting examples of persulfates, perborates, and percarbonates include ammonium persulfate, potassium persulfate, sodium persulfate, sodium perborate, potassium perborate, sodium percarbonate, and potassium percarbonate. Additional useful oxidizing agents include one or more of alkali metal bromates, ferricyanides, redox enzymes such as laccases, peroxidases, and 2-electron oxidoreductases, such as uricase.

These oxidizing agents may be used in place of the one or more oxidizing agents selected from the group consisting of persulfates, perborates, percarbonates, a salt thereof, and a mixture thereof, or these oxidizing agents may be combined with the one or more oxidizing agents selected from the group consisting of persulfates, perborates, percarbonates, a salt thereof, and a mixture thereof.

The total amount of oxidizing agents selected from the group consisting of persulfates, perborates, percarbonates, a salt thereof, and a mixture thereof in the transparent ready-to-use bleaching composition may vary but is typically about 10 to about 55 wt. %, based on the total weight of the transparent ready-to-use bleaching compositions. In some cases, the total amount of the oxidizing agents selected from the group consisting of persulfates, perborates, percarbonates, a salt thereof, and a mixture thereof, is about 10 to about 50 wt. %, about 10 to about 45 wt. %, about 10 to about 40 wt. %, about 10 to about 35 wt. %, about 15 to about 50 wt. %, about 15 to about 45 wt. %, about 15 to about 40 wt. %, or about 15 to about 35 wt. %, based on the total weight of the transparent ready-to-use bleaching composition.

Non-limiting examples of thickening agents include carboxylic acid/carboxylate copolymers, hydrophobically-modified cross-linked copolymers of carboxylic acid and alkyl carboxylate vinyl polymers, methyl cellulose, ethyl cellulose, hydroxyethyl cellulose, hydroxylpropyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, polyethyleneimine, bentonite, aluminum magnesium silicate, laponite, hectonite, anhydrous silicic acid, and a mixture thereof. In some cases, the one or more thickening agents are selected from the group consisting of methyl cellulose, ethyl cellulose, hydroxyethyl cellulose, hydroxypropyl methyl cellulose, hydroxylpropyl cellulose, sodium carboxymethyl cellulose, polyvinylpyrrolidone, polyvinyl alcohol, guar gum, hydroxypropyl guar gum, xanthan gum, arabic gum, carrageenan, starch-based polymers, and a mixture thereof. Furthermore, in some cases, non-acrylic thickening agents that are useful in the instant compositions include xanthan gum, cellulose gum, guar gum, algin, chitosan, hydroxyethylcellulose, hydroxypropylcellulose, cetyl hydroxyethylcellulose, polyvinylpyrrolidone, and a mixture thereof. In some cases, xanthan gum is particularly useful. Separately, in some cases it may be desirable to exclude cellulose thickening agents, such as cellulose gum.

The total amount of the one or more non-acrylic thickening agents in the transparent ready-to-use bleaching composition may vary but is typically about 0.1 to about 10 wt. %, about 0.1 to about 8 wt. %, about 0.1 to about 6 wt. %, about 0.5 to about 10 wt. %, about 0.5 to about 8 wt. %, about 0.5 to about 6 wt. %, or about 1 to about 5 wt. %, based on the total weight of the transparent ready-to-use bleaching composition.

Non-limiting examples of acrylic polymers that are useful in the transparent ready-to-use bleaching compositions of the instant disclosure include crosslinked acrylic polymers. Non-limiting examples of crosslinked acrylic polymer include sodium polyacrylate, carbomer, acrylates C10-30 alkyl acrylate crosspolymer, or a mixture thereof. In some instances, the one or more acrylic polymers are crosslinked acrylic polymers. Crosslinked acrylic polymers can be selected from modified or unmodified carboxyvinyl polymers, such as copolymers of acrylic acid and of C10-C30 alkyl acrylate or methacrylate, for instance the products sold under the tradenames CARBOPOL and PEMULEN (INCI names: carbomer, acrylates/C10-30 alkyl acrylate crosspolymer) by the company Lubrizol, or such as the crosslinked sodium polyacrylate sold under the name COSMEDIA SP by the company Cognis (BASF) (INCI name: sodium polyacrylate). Among the crosslinked acrylic polymers, sodium polyacrylate, carbomer, and acrylates/C10-30 alkyl acrylate crosspolymer are useful. Also, the crosslinked acrylic polymer, sodium polyacrylate and/or acrylates/C10-30 alkyl acrylate crosspolymer are particularly useful.

The total amount of the one or more acrylic polymers that may be included in the transparent ready-to-use bleaching composition is about 0.1 to about 12 wt. %, about 0.1 to about 10 wt. %, about 0.1 to about 8 wt. %, about 0.1 to about 6 wt. %, about 1 to about 12 wt. %, about 1 to about 10 wt. %, about 1 to about 8 wt. %, or about 1 to about 6 wt. %, based on the total weight of the transparent ready-to-use hair bleaching composition.

The transparent ready-to-use bleaching compositions may include one or more ammonium salts. Non-limiting examples of ammonium salts include ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate, ammonium lactate, and a mixture thereof.

The total amount of one or more ammonium salts that may be included in a transparent ready-to-use bleaching composition may vary but is typically about 0.1 to about 10 wt. %, based on the total weight of the transparent ready-to-use bleaching composition. In some cases, the total amount of the one or more ammonium salts is about 0.1 to about 8 wt. %, about 0.1 to about 6 wt. %, about 0.1 to about 4 wt. %, or about 0.1 to about 2 wt. %, based on the total weight of the transparent ready-to-use bleaching composition.

Additionally, the transparent ready-to-use bleaching compositions may optionally include one or more alkaline agents other than the one or more ammonium salts (discussed above). Non-limiting examples include carbonates such as potassium carbonate and sodium hydrogencarbonate, alkanolamines, organic amines, a basic amino acid, and salts thereof. Non-limiting examples of an alkanolamine include monoethanolamine and triethanolamine. Non-limiting examples of an organic amine include 2-amino-2-methyl-1-propanol (AMP), 2-amino-2-methyl-1,3-propanediol, and guanidine. Non-limiting examples of basic amino acids include arginine and lysine. In some cases, carbonates, such as potassium carbonate are particularly useful.

The total amount of the one or more alkaline agents other than the one or more ammonium salts that may be included in a transparent ready-to-use bleaching composition may vary but is typically about 0.1 to about 10 wt. %, based on the total amount of the transparent ready-to-use bleaching composition. In some cases, the total amount of the one or more alkaline agents other than the one or more ammonium salts in the transparent ready-to-use bleaching composition is about 0.1 to about 8 wt. %, about 0.1 to about 6 wt. %, about 0.1 to about 5 wt. %, about 0.1 to about 4 wt. %, about 0.5 to about 10 wt. %, about 0.5 to about 8 wt. %, about 0.5 to about 6 wt. %, about 0.5 to about 5 wt. %, or about 0.5 to about 4 wt. % based on the total weight of the transparent ready-to-use bleaching composition.

In some instances, the transparent ready-to-use bleaching compositions include one or more oils. The one or more oils typically include those generally used in cosmetics and particularly from oils of animal, vegetable or mineral origin, linear or branched hydrocarbons, optionally branched and/or unsaturated fatty acids, optionally branched and/or unsaturated fatty alcohols, mono- and/or polyesters of fatty acids and/or of fatty alcohols, perfluorinated and/or orgaofluorinated oils, volatile or non-volatile silicone oils, fluorosilicone oils and their mixtures. Mention is made, as an example of linear or branched hydrocarbons, of oils of mineral or synthetic origin, such as liquid paraffins and their derivatives, petrolatum, mineral oils, (mixtures of oil-derived hydrocarbon oils), polybutene, hydrogenated polyisobutene, polyisoprene, polydecenes such as hydrogenated polydecene, or also linear, branched and/or cyclic alkanes which are optionally volatile, such as, for example, isohexadecane, isododecane, isodecane or isohexadecane, and their mixtures.

The total amount of the one or more oils that may be included in a transparent ready-to-use bleaching composition may vary but is typically about 0.1 to about 10 wt. %, based on the total weight of the transparent ready-to-use bleaching composition. In some cases, the total amount of the one or more oils may be about 0.1 to about 8 wt. %, about 0.1 to about 6 wt. %, about 0.1 to about 4 wt. %, or about 0.1 to about 2 wt. %, based on the total weight of the transparent ready-to-use bleaching composition.

The transparent ready-to-use bleaching compositions may also include one or more silicates. Non-limiting examples of silicates include lithium, sodium, and potassium silicates, metasilicates and disilicates, and a combination thereof, including mixed lithium, sodium, and potassium salts thereof. Specific non-limiting examples include aluminum silicate, magnesium silicate, aluminum magnesium silicate, calcium silicate, barium silicate, strontium silicate, and a mixture thereof.

The total amount of the one or more silicates that may be included may vary but is typically about 1 to about 50 wt. % based on the total weight of the transparent ready-to-use bleaching composition. In some cases, the total amount of the one or more silicates is about 1 to about 40 wt. %, about 5 to about 50 wt. %, about 5 to about 40 wt. %, about 10 to about 10 wt. %, about 15 to about 50 wt. %, about 15 to about 40 wt. %, about 20 to about 50 wt. %, or about 20 to about 40 wt. %, based on the total weight of the transparent ready-to-use bleaching composition.

The total amount of hydrogen peroxide in the transparent ready-to-use bleaching composition can vary but is typically about 1 to about 30 wt. %, based on the total weight of the transparent ready-to-use bleaching composition. For instance, the total amount of the hydrogen peroxide may be about 1 to about 25 wt. %, about 1 to about 20 wt. %, about 1 to about 15 wt. %, about 1 to about 10 wt. %, about 2 to about 30 wt. %, about 2 to about 25 wt. %, about 2 to about 20 wt. %, about 2 to about 15 wt. %, or about 2 to about 10 wt. %, based on the total weight of the transparent ready-to-use bleaching composition.

Particularly useful polyurethane polyethers that may be included in the transparent ready-to-use bleaching compositions include polyoxyethylenated polyurethane polyethers. A non-limiting example of a polyoxyethylenated polyurethane polyether includes disteareth-100 IPDI. Also useful are polyurethane polyethers comprising in their chain both hydrophilic blocks usually of polyoxyethylenated nature and hydrophobic blocks, which may be aliphatic sequences alone and/or cycloaliphatic and/or aromatic sequences (e.g., nonionic fatty-chain polyurethane polyethers). In some instances, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. Furthermore, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

Nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane linkage between the hydrophilic blocks, whence arises the name. By extension, also included among the nonionic fatty-chain polyurethane polyethers are those in which the hydrophilic blocks are linked to the lipophilic blocks via other chemical bonds. As examples of nonionic fatty-chain polyurethane polyethers that may be used in the invention, it is also possible to use RHEOLATE 205 containing a urea function, sold by the company Rheox, or RHEOLAT. 208, 204 or 212, and also ACRYSOL 84. Mention may also be made of the product ELFACOS T210 containing a $C_{12-14}$ alkyl chain, and the product ELFACOS T212 containing a $C_{18}$ alkyl chain, from Akzo.

The product DW 1206B from Rohm & Haas containing a $C_{20}$ alkyl chain and a urethane linkage, sold at a solids content of 20% in water, may also be used. It is also possible to use solutions or dispersions of these polymers, especially in water or in aqueous-alcoholic medium. Examples of such polymers that may be mentioned are RHEOLATE 255, RHEOLATE 278 and RHEOLATE 244 sold by the company Rheox. The products DW 1206F and DW 1206J sold by the company Rohm & Haas may also be used.

The polyurethane polyethers that may be used include those described in the article by G. Fonnum, J. Bakke and Fk. Hansen-Colloid Polym. Sci 271, 380.389 (1993), which is incorporated herein by reference in its entirety.

In some cases, it may be useful to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate. Such polyurethane polyethers are sold especially by the company Rohm & Haas under the names ACULYN 46 and ACULYN 44. ACULYN 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%). ACULYN 44 is a polycondensate of polyethylene glycol containing 150 or 180 mol of ethylene oxide, of decyl alcohol and of methylenebis(4-cyclohexyl-isocyanate) (SMDI), at 35% by weight in a mixture of propylene glycol (39%) and water (26%).

The total amount of the one or more polyurethane polyethers in the transparent ready-to-use bleaching composition may vary but is typically about 0.1 to about 20 wt. %, based on the total weight of the transparent ready-to-use bleaching composition. In some cases, the total amount of the one or more polyurethane polyethers is about 0.1 to about 15 wt. %, about 0.1 to about 10 wt. %, about 0.1 to about 5 wt. %, about 0.5 to about 20 wt. %, about 0.5 to about 15 wt. %, about 0.5 to about 10 wt. %, about 0.5 to about 5 wt. %, about 1 to about 20 wt. %, about 1 to about 15 wt. %, about 1 to about 10 wt. %, or about 1 to about 5 wt. %, based on the total weight of the transparent ready-to-use bleaching composition.

In some cases, the transparent ready-to-use bleaching composition may include one or more surfactants such as one or more nonionic, anionic, cationic, or amphoteric surfactants. In some instances, nonionic surfactants are useful. The total amount of one or more surfactants may vary but is typically about 0.01 to about 15 wt. %, based on the total amount of the transparent ready-to-use bleaching composition. In some cases, the total amount of the one or more surfactants is about 0.01 to about 10 wt. %, about 0.01 to about 5 wt. %, about 0.5 to about 10 wt. %, about 0.5 to about 5 wt. %, about 1 to about 10 wt. %, or about 1 to about 5 wt. %, based on the total weight of the transparent ready-to-use bleaching composition.

Non-limiting examples of nonionic surfactants that may be useful include polyoxyalkylenated or polyglycerolated nonionic surfactants. The oxyalkylene units are more particularly oxyethylene or oxypropylene units, or a combination thereof, and are preferably oxyethylene units. Non-limiting examples of oxyalkylenated nonionic surfactants that may be mentioned include: oxyalkylenated ($C_8$-$C_{24}$) alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

With respect amounts nonionic surfactants, the total amount of nonionic surfactants that may be included in a transparent ready-to-use bleaching composition may be, for example, about 0.01 to about 10 wt. %, based on the total weight of the transparent ready-to-use bleaching composition. In some cases, the total amount of the one or more nonionic surfactants is about 0.01 to about 8 wt. %, about 0.01 to about 5 wt. %, about 0.01 to about 4 wt. %, or about 0.01 to about 2 wt. %, based on the total weight of the transparent ready-to-use bleaching composition.

The total amount of water in the transparent ready-to-use hair bleaching composition can vary but is typically about 20 to about 80 wt. %, based on the total weight of the transparent ready-to-use bleaching composition. The total amount of water in the transparent ready-to-use bleaching composition, however, may be about 25 to about 75 wt. %, about 25 to about 70 wt. %, about 25 to about 65 wt. %, about 25 to about 60 wt. %, about 30 to about 80 wt. %, about 30 to about 75 wt. %, about 30 to about 70 wt. %, about 30 to about 65 wt. %, or about 30 to about 60 wt. %, based on the total weight of the transparent ready-to-use bleaching composition.

The composition described herein (bleach compositions, developer compositions, and/or transparent ready-to-use compositions) may contain or exclude one or more cosmetically acceptable excipients. Cosmetically acceptable excipients that may be included or excluded include, but are not limited to preservatives, antioxidants, chelating agents, sunscreen agents, vitamins, dyes, hair coloring agents, proteins, amino acids, natural extracts such as plant extracts, humectants, fragrances, perfumes, oils, emollients, lubricants, butters, penetrants, hair fixatives, film formers, detergents, volatiles, propellants, pH adjusting agents (e.g., citric acid), neutralizing agents, buffers, hair conditioning agents, anti-static agents, anti-frizz agents, anti-dandruff agents, absorbents, and a combination thereof.

The composition of the disclosure (bleach compositions, developer compositions, and/or transparent ready-to-use compositions) may be provided in any suitable physical form. Suitable forms include, but are not limited to low to moderate viscosity liquids, lotions, milks, mousses, sprays, gels, creams, shampoos, conditioners, and the like.

The transparent ready-to-use bleaching composition may optionally include colorants and/dyes, provided that the colorants and/or dyes do not negate the transparency of the composition, e.g., provided that the composition has a transmittance of at least 80% at a wavelength of 600 nm, for example measured using a Lambda 40 UV-visible spectrometer, at a concentration of 0.5% by weight in water. Useful colorants are those that are stable in the hair bleaching compositions. These colorants can be used, for example, to impart toning and coloring to hair. Non-limiting colorants include pigments, liposoluble dyes, direct dyes, oxidative dye precursors, nacreous pigments, pearling agents, leuco dyes, optical lightening colorants, natural colorants and optically-variable pigments.

In certain embodiments, the transparent ready-to-use hair bleaching compositions of the instant disclosure include:
   i. about 5 to about 50 wt. %, about 10 to about 40 wt. %, or about 15 to about 40 wt. % of one or more oxidizing agents selected from the group consisting of persulfates, perborates, percarbonates, a salt thereof, and a mixture thereof;
   ii. about 0.1 to about 6 wt. %, about 0.5 to about 5 wt. %, or about 1 to about 5 wt. % of one or more non-acrylic thickening agents;
   iii. about 0.1 to about 10 wt. %, about 1 to about 10 wt. %, or about 1 to about 6 wt % of one or more acrylic polymers;
   iv. about 1 to about 40 wt. %, about 1 to about 30 wt. %, or about 5 to about 25 wt. % of hydrogen peroxide;
   v. about 0.1 to about 20 wt. %, about 0.1 to about 15 wt. %, or about 1 to about 10 wt. % of one or more polyurethane polyethers; and
   vi. water.

The transparent ready-to-use bleaching compositions of the above embodiment may include one or more ammonium salts. Non-limiting examples of ammonium salts include ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate, ammonium lactate, and a mixture thereof.

The total amount of one or more ammonium salts that may be included may vary but is typically about 0.1 to about 10 wt. %, based on the total weight of the transparent ready-to-use bleaching composition. In some cases, the total amount of the one or more ammonium salts is about 0.1 to about 8 wt. %, about 0.1 to about 6 wt. %, about 0.1 to about 4 wt. %, or about 0.1 to about 2 wt. %, based on the total weight of the transparent ready-to-use bleaching composition.

Additionally, the transparent ready-to-use bleaching compositions of the above embodiment may include one or more alkaline agents other than the one or more ammonium salts (discussed above). Non-limiting examples include carbonates such as potassium carbonate and sodium hydrogencarbonate, alkanolamines, organic amines, a basic amino acid, and salts thereof. Non-limiting examples of an alkanolamine include monoethanolamine and triethanolamine. Non-limiting examples of an organic amine include 2-amino-2-methyl-1-propanol (AMP), 2-amino-2-methyl-1,3-propanediol, and guanidine. Non-limiting examples of basic amino acids include arginine and lysine. In some cases, carbonates, such as potassium carbonate are particularly useful.

The total amount of the one or more alkaline agents other than the one or more ammonium salts that may be included can vary but is typically about 0.1 to about 10 wt. %, based on the total amount of the transparent ready-to-use bleaching composition. In some cases, the total amount of the one or more alkaline agents other than the one or more ammonium salts in the transparent ready-to-use bleaching composition is about 0.1 to about 8 wt. %, about 0.1 to about 6 wt. %, about 0.1 to about 5 wt. %, about 0.1 to about 4 wt. %, about 0.5 to about 10 wt. %, about 0.5 to about 8 wt. %, about 0.5 to about 6 wt. %, about 0.5 to about 5 wt. %, or about 0.5 to about 4 wt. % based on the total weight of the transparent ready-to-use bleaching composition.

The transparent ready-to-use bleaching composition of the above embodiment may include one or more oils. The one or more oils typically include those generally used in cosmetics and particularly from oils of animal, vegetable or mineral origin, linear or branched hydrocarbons, optionally branched and/or unsaturated fatty acids, optionally branched and/or unsaturated fatty alcohols, mono- and/or polyesters of fatty acids and/or of fatty alcohols, perfluorinated and/or orgaofluorinated oils, volatile or non-volatile silicone oils, fluorosilicone oils and their mixtures. Mention is made, as an example of linear or branched hydrocarbons, of oils of mineral or synthetic origin, such as liquid paraffins and their derivatives, petrolatum, mineral oils, (mixtures of oil-derived hydrocarbon oils), polybutene, hydrogenated polyisobutene, polyisoprene, polydecenes such as hydrogenated polydecene, or also linear, branched and/or cyclic alkanes which are optionally volatile, such as, for example, isohexadecane, isododecane, isodecane or isohexadecane, and their mixtures.

The total amount of the one or more oils that may be included may vary but is typically about 0.1 to about 10 wt. %, based on the total weight of the transparent ready-to-use bleaching composition. In some cases, the total amount of the one or more oils may be about 0.1 to about 8 wt. %, about 0.1 to about 6 wt. %, about 0.1 to about 4 wt. %, or about 0.1 to about 2 wt. %, based on the total weight of the transparent ready-to-use bleaching composition.

The transparent ready-to-use bleaching composition of the above embodiment may include one or more silicates. Non-limiting examples of silicates u include lithium, sodium, and potassium silicates, metasilicates and disilicates, and a combination thereof, including mixed lithium, sodium, and potassium salts thereof. Specific non-limiting examples include aluminum silicate, magnesium silicate, aluminum magnesium silicate, calcium silicate, barium silicate, strontium silicate, and a mixture thereof.

The total amount of the one or more silicates that may be about 1 to about 50 wt. % based on the total weight of the transparent ready-to-use bleaching composition. In some cases, the total amount of the one or more silicates is about 1 to about 40 wt. %, about 5 to about 50 wt. %, about 5 to about 40 wt. %, about 10 to about 10 wt. %, about 15 to about 50 wt. %, about 15 to about 40 wt. %, about 20 to about 50 wt. %, or about 20 to about 40 wt. %, based on the total weight of the transparent ready-to-use bleaching composition.

The total amount of water in the transparent ready-to-use hair bleaching composition can vary but is typically about 20 to about 80 wt. %, based on the total weight of the transparent ready-to-use bleaching composition. The total amount of water in the transparent ready-to-use bleaching composition, however, may be about 25 to about 75 wt. %, about 25 to about 70 wt. %, about 25 to about 65 wt. %, about 25 to about 60 wt. %, about 30 to about 80 wt. %, about 30 to about 75 wt. %, about 30 to about 70 wt. %, about 30 to about 65 wt. %, or about 30 to about 60 wt. %, based on the total weight of the transparent ready-to-use bleaching composition.

In certain embodiments, the transparent ready-to-use hair bleaching compositions of the instant disclosure include:
 i. about 5 to about 50 wt. %, about 10 to about 40 wt. %, or about 15 to about 40 wt. % of one or more oxidizing agents selected from the group consisting of persulfates, perborates, percarbonates, a salt thereof, and a mixture thereof;
 ii. about 0.1 to about 6 wt. %, about 0.5 to about 5 wt. %, or about 1 to about 5 wt. % of xanthan gum;
 iii. about 0.1 to about 10 wt. %, about 1 to about 10 wt. %, or about 1 to about 6 wt % of one or more acrylic polymers, for example, one or more acrylic polymers selected from the group consisting of sodium polyacrylate, carbomer, acrylates C10-30 alkyl acrylate crosspolymer, or a mixture thereof;
 iv. about 1 to about 40 wt. %, about 1 to about 30 wt. %, or about 5 to about 25 wt. % of hydrogen peroxide;
 v. about 0.1 to about 20 wt. %, about 0.1 to about 15 wt. %, or about 1 to about 10 wt. % of one or more polyurethane polyethers, for example, disteareth-100 IPDI;
 vi. one or more oils, for example, about 0.1 to about 20 wt. %, about 0.1 to about 10 wt. %, or about 0.1 to about 5 wt. % of an oil selected from the group consisting of polybutene, hydrogenated polyisobutene, polyisoprene, polydecenes such as hydrogenated polydecene, and a mixture thereof;
 vii. one or more silicates; and
 viii. water.

The transparent ready-to-use bleaching compositions of the above embodiment may include one or more ammonium salts. Non-limiting examples of ammonium salts include ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate, ammonium lactate, and a mixture thereof.

The total amount of one or more ammonium salts that may be included may vary but is typically about 0.1 to about 10 wt. %, based on the total weight of the transparent ready-to-use bleaching composition. In some cases, the total amount of the one or more ammonium salts is about 0.1 to about 8 wt. %, about 0.1 to about 6 wt. %, about 0.1 to about 4 wt. %, or about 0.1 to about 2 wt. %, based on the total weight of the transparent ready-to-use bleaching composition.

Additionally, the transparent ready-to-use bleaching compositions of the above embodiment may include one or more alkaline agents other than the one or more ammonium salts (discussed above). Non-limiting examples include carbonates such as potassium carbonate and sodium hydrogencarbonate, alkanolamines, organic amines, a basic amino acid, and salts thereof. Non-limiting examples of an alkanolamine include monoethanolamine and triethanolamine. Non-limiting examples of an organic amine include 2-amino-2-methyl-1-propanol (AMP), 2-amino-2-methyl-1,3-propanediol, and guanidine. Non-limiting examples of basic amino acids include arginine and lysine. In some cases, carbonates, such as potassium carbonate are particularly useful.

The total amount of the one or more alkaline agents other than the one or more ammonium salts that may be included can vary but is typically about 0.1 to about 10 wt. %, based on the total amount of the transparent ready-to-use bleaching composition. In some cases, the total amount of the one or more alkaline agents other than the one or more ammonium salts in the transparent ready-to-use bleaching composition is about 0.1 to about 8 wt. %, about 0.1 to about 6 wt. %, about 0.1 to about 5 wt. %, about 0.1 to about 4 wt. %, about 0.5 to about 10 wt. %, about 0.5 to about 8 wt. %, about 0.5 to about 6 wt. %, about 0.5 to about 5 wt. %, or about 0.5 to about 4 wt. % based on the total weight of the transparent ready-to-use bleaching composition.

The one or more oils typically include those generally used in cosmetics and particularly from oils of animal, vegetable or mineral origin, linear or branched hydrocarbons, optionally branched and/or unsaturated fatty acids, optionally branched and/or unsaturated fatty alcohols, mono- and/or polyesters of fatty acids and/or of fatty alcohols, perfluorinated and/or orgaofluorinated oils, volatile or non-volatile silicone oils, fluorosilicone oils and their mixtures. Mention is made, as an example of linear or branched hydrocarbons, of oils of mineral or synthetic origin, such as liquid paraffins and their derivatives, petrolatum, mineral oils, (mixtures of oil-derived hydrocarbon oils), polybutene, hydrogenated polyisobutene, polyisoprene, polydecenes such as hydrogenated polydecene, or also linear, branched and/or cyclic alkanes which are optionally volatile, such as, for example, isohexadecane, isododecane, isodecane or isohexadecane, and their mixtures.

The total amount of the one or more oils that may be included may vary but is typically about 0.1 to about 10 wt. %, based on the total weight of the transparent ready-to-use bleaching composition. In some cases, the total amount of the one or more oils may be about 0.1 to about 8 wt. %, about 0.1 to about 6 wt. %, about 0.1 to about 4 wt. %, or about 0.1 to about 2 wt. %, based on the total weight of the transparent ready-to-use bleaching composition.

Non-limiting examples of silicates useful in the above embodiment include lithium, sodium, and potassium silicates, metasilicates and disilicates, and a combination thereof, including mixed lithium, sodium, and potassium salts thereof. Specific non-limiting examples include aluminum silicate, magnesium silicate, aluminum magnesium silicate, calcium silicate, barium silicate, strontium silicate, and a mixture thereof.

The total amount of the one or more silicates that may be about 1 to about 50 wt. % based on the total weight of the transparent ready-to-use bleaching composition. In some cases, the total amount of the one or more silicates is about 1 to about 40 wt. %, about 5 to about 50 wt. %, about 5 to about 40 wt. %, about 10 to about 10 wt. %, about 15 to about 50 wt. %, about 15 to about 40 wt. %, about 20 to about 50 wt. %, or about 20 to about 40 wt. %, based on the total weight of the transparent ready-to-use bleaching composition.

The total amount of water in the transparent ready-to-use hair bleaching composition can vary but is typically about 20 to about 80 wt. %, based on the total weight of the transparent ready-to-use bleaching composition. The total amount of water in the transparent ready-to-use bleaching composition, however, may be about 25 to about 75 wt. %, about 25 to about 70 wt. %, about 25 to about 65 wt. %, about 25 to about 60 wt. %, about 30 to about 80 wt. %, about 30 to about 75 wt. %, about 30 to about 70 wt. %, about 30 to about 65 wt. %, or about 30 to about 60 wt. %, based on the total weight of the transparent ready-to-use bleaching composition.

The instant disclosure also relates to kits, which typically include a bleach composition and a developer composition, wherein the bleach composition and the developer composition are separately packaged or contained. When the bleach composition and developer composition are combined, a transparent ready-to-use composition is formed. Instructions, mixing components, brushes, gloves, measuring tools, etc., may also be included in the kits.

The various compositions of the disclosure and the kits are useful in methods for bleaching hair (or lightening hair or coloring hair). The methods typically include applying a transparent ready-to-use bleaching composition to hair; allowing the composition to remain on the hair for a period of time; and rinsing the composition from the hair. The methods may further include obtaining a bleach composition and a developer composition of the instant disclosure, and combining the compositions to derive a transparent ready-to-use bleaching composition, which can then be used in methods for bleaching hair.

More exhaustive but non-limiting lists of components useful in the compositions disclosed herein are provided below.

Oils

The one or more oils typically include those generally used in cosmetics and particularly from oils of animal, vegetable or mineral origin, linear or branched hydrocarbons, optionally branched and/or unsaturated fatty acids, optionally branched and/or unsaturated fatty alcohols, mono- and/or polyesters of fatty acids and/or of fatty alcohols, perfluorinated and/or organofluorinated oils, volatile or non-volatile silicone oils, fluorosilicone oils and their mixtures.

Non-limiting examples of oils include oils of animal, vegetable or mineral origin, of lanolin, squalene, fish oil, perhydrosqualene, mink oil, turtle oil, soybean oil, grape seed oil, sesame oil, maize oil, rapeseed oil, sunflower oil, cottonseed oil, avocado oil, olive oil, castor seed oil, jojoba seed oil, peanut oil, sweet almond oil, palm oil, cucumber oil, hazelnut oil, apricot kernel oil, wheat germ oil, calophyllum oil, macadamia oil, coconut oil, cereal germ oil, candlenut oil, thistle oil, candelilla oil, safflower oil, shea butter, and their mixtures.

Mention is made, as an example of linear or branched hydrocarbons, of oils of mineral or synthetic origin, such as liquid paraffins and their derivatives, petrolatum, mineral oils, (mixtures of oil-derived hydrocarbon oils), polybutene, hydrogenated polyisobutene, polyisoprene, polydecenes such as hydrogenated polydecene, or also linear, branched and/or cyclic alkanes which are optionally volatile, such as, for example, isohexadecane, isododecane, isodecane or isohexadecane, and their mixtures.

Mention is made, as examples of optionally branched and/or unsaturated fatty acids, of myristic acid, palmitic acid, stearic acid, behenic acid, oleic acid, linoleic acid, linolenic acid or isostearic acid, and their mixtures.

Mention is made, as example of optionally branched and/or unsaturated fatty alcohols, of cetanol, stearyl alcohol, oleyl alcohol, cetyl alcohol, octyldodecanol, and their mixtures.

Mention is made, as examples of esters, of monoesters or polyesters of fatty acids, the linear or branched fatty chain of which includes from 6 to 30 carbon atoms, and of fatty alcohols, the fatty chain of which includes from 3 to 30 carbon atoms, in particular mono- and polyesters of hydroxy acids and of fatty alcohols, esters of benzoic acid and of fatty alcohols, polyesters of polyols, dipentaerythrityl $C_5$-$C_9$ esters, trimethylolpropane polyesters, propylene glycol polyesters, polyesters of hydrogenated castor oil.

Further mention is made of the oils of the group consisting of isononyl isononanoate, stearyl octanoate, isopropyl palmitate, isopropyl myristate, butyl stearate, hexyl laurate, 2-ethylhexyl palmitate, 2-hexyldecyl laurate, 2-octyldecyl palmitate, 2-octyldodecyl myristate, di(2-ethylhexyl) succinate, diisostearyl malate, 2-octyldodecyl lactate, glyceryl triisostearate or diglyceryl triisostearate, octyldodecyl stearoyl stearate (Ceraphyl), cetearyl isononanoate, diisopropyl adipate, caprylic/capric triglyceride, glyceryl tricaprate/caprylate, isocetyl stearoyl stearate, $C_{12}$-$C_{15}$ alkyl benzoates, pentaerythrityl tetraisostearate, dipentaerythrityl pentaisononanoate, bis-diglyceryl polyacyladipate-2, trimethylolpropane triethylhexanoate, propylene glycol dibenzoate, propylene glycol dioctanoate, and mixture thereof.

Mention is made, as example of volatile silicone oils, of hexamethyldisiloxane, dimethicones with a viscosity of between 0.65 and 5 mm²/s, octamethylcyclotetrasiloxane, heptamethylhexyltrisiloxane, decamethylcyclopentasiloxane, decamethyltetrasiloxane, octamethyltrisiloxane, dodecamethylcyclohexasiloxane, heptamethyloctyltrisiloxane, and their mixtures.

Mention is made, as example of non-volatile silicone oils, of non-volatile polydialkylsiloxanes; polydimethylsiloxanes comprising pendant alkyl, alkoxy or phenyl groups or alkyl, alkoxy or phenyl groups at the end of the silicone chain, which groups have from 2 to 24 carbon atoms; phenylated silicones, such as those of the phenyl trimethicone type, those of the phenylpropyldimethylsiloxysilicate type or those of the trimethylpentaphenyltrisiloxane type; polysiloxanes modified by fatty acids, in particular $C_8$-$C_{20}$ fatty acids, fatty alcohols, in particular $C_8$-$C_{20}$ fatty alcohols, or polyoxyalkylenes (in particular polyoxyethylene and/or polyoxypropylene); aminated polysiloxanes; polysiloxanes comprising a hydroxyl group; and their mixtures.

Mention is made, as fluorosilicone oils, of fluorinated polysiloxanes comprising a pendant fluorinated group or a fluorinated group at the end of the silicone chain having from 1 to 12 carbon atoms, all or a portion of the hydrogens of which are replaced by fluorine atoms, such as perfluorononyl dimethicone, and their mixtures.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The preservative is optionally included in an amount ranging from about 0.01 wt. % to about 5 wt. %, about 0.15% to about 1 wt. %, or about 1 wt. % to about 3 wt. %, based on the total weight of the composition.

Suitable components, such as those listed above, are included or excluded from the hair care formulations depending on the specific combination of other components, the form of the compositions, and/or the use of the formulation (e.g., hair spray, cream, conditioner, etc.).

Non-Ionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and a mixture thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

Examples of oxyalkylenated nonionic surfactants that may be mentioned include: [0115] oxyalkylenated ($C_8$-$C_{24}$) alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

The surfactants preferably contain a number of moles of ethylene oxide and/or of propylene oxide of between 2 and 100 and most preferably between 2 and 50. Advantageously, the nonionic surfactants do not comprise any oxypropylene units.

In accordance with one preferred embodiment of the invention, the oxyalkylenated nonionic surfactants are chosen from oxyethylenated $C_8$-$C_{30}$ alcohols.

Examples of ethoxylated fatty alcohols (or $C_8$-$C_{30}$ alcohols) that may be mentioned include the adducts of ethylene oxide with lauryl alcohol, especially those containing from 9 to 50 oxyethylene groups and more particularly those containing from 10 to 25 oxyethylene groups (Laureth-10 to Laureth-25); the adducts of ethylene oxide with behenyl alcohol, especially those containing from 9 to 50 oxyethylene groups (Beheneth-9 to Beheneth-50); the adducts of ethylene oxide with cetearyl alcohol (mixture of cetyl alcohol and stearyl alcohol), especially those containing from 10 to 30 oxyethylene groups (Ceteareth-10 to Ceteareth-30); the adducts of ethylene oxide with cetyl alcohol, especially those containing from 10 to 30 oxyethylene groups (Ceteth-10 to Ceteth-30); the adducts of ethylene oxide with stearyl alcohol, especially those containing from 10 to 30 oxyethylene groups (Steareth-10 to Steareth-30); the adducts of ethylene oxide with isostearyl alcohol, especially those containing from 10 to 50 oxyethylene groups (Isosteareth-10 to Isosteareth-50); and a mixture thereof.

As examples of polyglycerolated nonionic surfactants, polyglycerolated $C_8$-$C_{40}$ alcohols are preferably used.

In particular, the polyglycerolated $C_8$-$C_{40}$ alcohols correspond to the following formula:

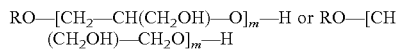

$$RO\text{—}[CH_2\text{—}CH(CH_2OH)\text{—}O]_m\text{—}H \text{ or } RO\text{—}[CH(CH_2OH)\text{—}CH_2O]_m\text{—}H$$

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

According to one of the embodiments according to the present invention, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and a mixture thereof.

Examples of ethoxylated fatty esters that may be mentioned include the adducts of ethylene oxide with esters of lauric acid, palmitic acid, stearic acid or behenic acid, and a mixture thereof, especially those containing from 9 to 100 oxyethylene groups, such as PEG-9 to PEG-50 laurate; PEG-9 to PEG-50 palmitate; PEG-9 to PEG-50 stearate; PEG-9 to PEG-50 palmitostearate; PEG-9 to PEG-50 behenate; polyethylene glycol 100 EO monostearate; and a mixture thereof.

As glyceryl esters of fatty acids, glyceryl stearate (glyceryl mono-, di- and/or tristearate) (glyceryl stearate) or glyceryl ricinoleate and a mixture thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Croda, and a product containing glyceryl stearate (glyceryl mono- and distearate) and potassium stearate, can also be used.

The sorbitol esters of $C_8$-$C_{24}$ fatty acids and alkoxylated derivatives thereof can be selected from sorbitan palmitate, sorbitan trioleate and esters of fatty acids and alkoxylated sorbitan containing for example from 20 to 100 EO, such as for example polyethylene sorbitan trioleate (polysorbate 85) or the compounds marketed under the trade names Tween 20 or Tween 60 by Croda.

As esters of fatty acids and glucose or alkylglucose, in particular glucose palmitate, alkylglucose sesquistearates such as methylglucose sesquistearate, alkylglucose palmitates such as methylglucose or ethylglucose palmitate, methylglucoside fatty esters and more specifically the diester of methylglucoside and oleic acid (Methyl glucose dioleate), the mixed ester of methylglucoside and the mixture oleic acid/hydroxystearic acid (Methyl glucose dioleate/hydroxystearate), the ester of methylglucoside and isostearic acid (Methyl glucose isostearate), the ester of methylglucoside and lauric acid (Methyl glucose laurate), the mixture of monoester and diester of methylglucoside and isostearic acid (Methyl glucose sesqui-isostearate), the mixture of monoester and diester of methylglucoside and stearic acid (Methyl glucose sesquistearate) and in particular the product marketed under the name Glucate SS by Lubrizol, and a mixture thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (PEG-20 methyl glucose distearate) such as the product marketed under the name GLUCAM E-20 DISTEARATE by Lubrizol, the polyethylene glycol ether of the mixture of monoester and diester of methylglucose and stearic acid with about 20 moles of ethylene oxide (PEG-20 methyl glucose sesquistearate) and in particular the product marketed under the name GLUCAMATE SSE-20 by Lubrizol, and a mixture thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLATAREN 2000 by BASF, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by BASF, cocoglucoside such as the product marketed under the name PLANTACARE 818/UP by BASF, cetostearyl glucoside possibly mixed with cetostearyl alcohol, marketed for example under the name MONTANOV 68 by Seppic, under the name TEGO-CARE CG90 by Evonik, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and a mixture thereof can in particular be cited.

Mixtures of glycerides of alkoxylated plant oils such as mixtures of ethoxylated (200 EO) palm and copra (7 EO) glycerides can also be cited.

It is preferable that the nonionic surfactant be selected from the group consisting of PEG-7 glyceryl cocoate, PEG-20 methylglucoside sesquistearate, PEG-20 glyceryl tri-isostearate, PG-5 dioleate, PG-4 diisostearate, PG-10 isostearate, PEG-8 isostearate, and PEG-60 hydrogenated castor oil.

Mixtures of these oxyethylenated derivatives of fatty alcohols and of fatty esters may also be used.

Preferably, the nonionic surfactant may be a nonionic surfactant with an HLB of 18.0 or less, such as from 4.0 to 18.0, more preferably from 6.0 to 15.0 and furthermore preferably from 9.0 to 13.0. The HLB is the ratio between the hydrophilic part and the lipophilic part in the molecule. This term HLB is well known to those skilled in the art and is described in "The HLB system. A time-saving guide to emulsifier selection" (published by ICI Americas Inc., 1984).

In some case, the nonionic surfactant is a fatty alkanolamide. Non-limiting examples of fatty alkanolamides that may be used include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

Cationic Conditioning Compounds

The cationic conditioning agents that may be included in the compositions of the instant disclosure include monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic conditioning agents are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryoloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases quaternized polymeric cationic conditioning agents are particularly useful. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 in the CTFA Cosmetic Ingredient Dictionary, 3rd Ed., published in 1982 by the Cosmetic Toiletry and Fragrance Association, Inc. (hereafter CTFA Dictionary and CTFA name), is sold under the trademark MERQUAT-100, and is described as having a weight average molecular weight of approximately 100,000. A copolymer reaction product of dimethyldiallylammonium chloride with acrylamide monomers is named Polyquaternium-7 in the CTFA Dictionary, is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the CTFA name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the CTFA name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10 in the CTFA Dictionary. Also useful are quaternized copolymers of hydroxyethylcellulose and dimethyldimethylammonium chloride, having the CTFA name Polyquaternium-4, sold in varying molecular weights under the trademark CELQUAT by National Starch and Chemical Corporation, Bridgewater, N.J.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconamidopropyldimethyl-2-hydroxyethyl-ammonium chloride and minkamidopropyldimethyl-2-hydroxyethylammonium chloride identified respectively by the CTFA names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the CTFA name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. Cocodimonium hydrolyzed animal protein, for example, is the CTFA name for a chemically-modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

Implementation of the present disclosure is provided by way of the following examples. The examples serve to illustrate the technology without being limiting in nature.

Example 1

Bleach Composition

| Bleach Powder | | |
|---|---|---|
| | INCI US Name | wt. % |
| Active | AMMONIUM PERSULFATE | 7 |
| | SODIUM PERSULFATE | 45 |
| Ammonium Salt | AMMONIUM SULFATE | 1 |
| Acrylic Polymer | ACRYLATES/C10-30 ALKYL ACRYLATE CROSSPOLYMER | 4 |
| Thickening Agent | XANTHAN GUM | 2.5 |
| Alkaline Agent | POTASSIUM CARBONATE | 3.25 |
| Oil | HYDROGENATED POLYDECENE | 0.75 |
| Silica | SILICA | 0.5 |
| Silicate | SODIUM SILICATE | 35 |
| Chelating agent | DISODIUM EDTA | 1 |
| Water | WATER | 0.01 |
| Total | | 100 |

Example 2

Developer Composition

| Developer | | |
|---|---|---|
| | INCI US Name | wt. % |
| Active | HYDROGEN PEROXIDE | 6 |
| | TETRASODIUM PYROPHOSPHATE | 0.04 |
| | TETRASODIUM ETIDRONATE | 0.1 |
| Polyurethane Polyether | DISTEARETH-100 IPDI | 3.4 |
| Nonionic Surfactant | STEARETH-100 | 0.1 |
| Preservative | SODIUM SALICATE | 0.04 |
| Water | WATER | 90.4 |
| Total | | 100 |

Example 3

Comparative Testing

Testing was carried out to assess the transparency of the compositions of the instant disclosure in comparison to the transparency of water and the transparency of a benchmark commercial product (BLONDME®—Schwarzkopf), which is advertised as a transparent bleaching composition. Transparency was determined based on the refractive index of the compositions using a Reichert AR200 digital Refractometer, model AR200, at 25° C.

|   | Description | Bleach Composition | Developer Composition | RI |
|---|---|---|---|---|
| A | DI Water | NA | NA | 1.333 |
| B | Bleach Composition of the Instant Disclosure (Example 1) with Commercially Available Developer (1:3 ratio) | Composition of Example 1 | Commercially Available Developer (20 V) Composition | 1.3554 |
| C | Bleach Composition of the Instant Disclosure (Example 1) with Developer Composition of the Instant Disclosure (Example 2) (1:3 ratio) | Composition of Example 1 | Developer Composition of Example 2 (20 V) | 1.3588 |
| D | BLONDME ® - Schwarzkopf Professional Kit (Benchmark) (1:3 ratio) | Commercially Available Beach Composition | Commercially Available Developer (20 V) | 1.3617 |

As shown above, the refractive index of water was found to be 1.33 (Test A), which is completely transparent. The compositions of Test B, C, and D were 1.36, which is very similar to water and very transparent. The results show that the inventive bleach compositions of the instant disclosure (e.g., Example 1) produce a transparent ready-to-use bleaching composition regardless of whether it is combined with a commercially available developer composition (shown in Test B) or whether it is combined with the developer compositions of the instant disclosure (e.g., Example 2) (shown in Test C). Finally, the data show that the inventive compositions (Test B and C) exceeded the transparency of the commercial benchmark product (BLONDME®-Schwarzkopf).

The compositions of Test C and D were further compared to each other. The difference in transparency between the composition of Test C and D could not be distinguished with the naked eye. The composition of Test C was initially thinner (more fluid-like in consistency) having more clumps than the composition of Test D, but after sitting for about 5 to 10 minutes, the composition of Test C thickened to have a similar consistency to the composition of Test D. Also, the clumps in the composition of Test C disappeared after sitting for about 5 to 10 minutes but the clumps in the composition of Test D did no disappear. The composition of Test C released more of a chemical odor than the composition of Test D but this difference may be due to the lack of fragrances in the composition of Test C. In terms of color lift, the composition of Test C provided about 3 and ¼ levels of lift on average, which was about ¼ level less lift than provided by the composition of Test D.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

Some of the various categories of components identified may overlap. For example, overlap may exist between some thickening agents and some cationic polymers. In such cases where overlap may exist and the composition includes both components (or the composition includes more than two components that overlap), an overlapping compound does not represent more than one component. For example, a homopolymer of methyl quaternized dimethylaminoethyl methacrylate crosslinked by a crosslinking agent may be considered both a cationic polymer and a thickening agent. If a particular composition includes both a cationic polymer component and a thickening agent component, a single homopolymer of methyl quaternized dimethylaminoethyl methacrylate crosslinked by a crosslinking agent will serve as only the cationic polymer or only the thickening agent (the compound does not serve as both the cationic polymer and the thickening agent).

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

The term "treat" (and its grammatical variations) as used herein refers to the application of the compositions of the present disclosure onto the surface of keratinous substrates such as hair. The term "treat," and its grammatical variations, relates to contacting hair with the compositions of the present disclosure.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A transparent ready-to-use hair bleaching composition formed by combining:
   (a) a bleach composition comprising:
      i. about 15 to about 45 wt. %, based on the total weight of the bleach composition, of one or more oxidizing agents chosen from persulfates, perborates, percarbonates, and a mixture thereof;
      ii. about 0.1 to about 5 wt. %, based on the total weight of the bleach composition, of xanthan gum;
      iii. about 0.1 to about 10 wt. %, based on the total weight of the bleach composition, of one or more acrylic polymers; and
      iv. one or more alkaline agents; and
   (b) a developer composition comprising:
      i. about 2 to about 20 wt. %, based on the total weight of the developer composition, of hydrogen peroxide;
      ii. about 0.1 to about 20 wt. %, based on the total weight of the developer composition, of disteareth-100 IPDI; and
      iii. water;
         wherein the composition has a pH above 7 and a refractory index of about 1.3 to about 1.4 at 25° C.

2. The transparent ready-to-use hair bleaching composition of claim 1, wherein the one or more acrylic polymers are chosen from sodium polyacrylate, a carbomer, acrylates C10-30 alkyl acrylate crosspolymer, and a mixture thereof.

3. The transparent ready-to-use hair bleaching composition of claim 1 comprising about 25 to about 75 wt. % of water, based on the total weight of the transparent ready-to-use hair bleaching composition.

4. A kit comprising:
   (a) a bleach composition comprising:
      i. one or more oxidizing agents chosen from persulfates, perborates, percarbonates, and a mixture thereof;
      ii. xanthan gum; and
      iii. one or more acrylic polymers; and
   (b) a developer composition comprising:
      i. hydrogen peroxide;
      ii. disteareth-100 IPDI; and
      iii. water;
         wherein the bleach composition of (a) and the developer composition of (b) are separately contained, and
         the bleach composition of (a) and the developer composition of (b) form a transparent ready-to-use hair bleaching composition having a refractory index of about 1.3 to about 1.4 at 25° C. and a pH above 7 when combined in a weight ratio of about 1:5 to about 5:1.

5. A bleach composition comprising:
   i. one or more oxidizing agents chosen from persulfates, perborates, percarbonates, and a mixture thereof;
   ii. xanthan gum;
   iii. one or more acrylic polymers;
   iv. one or more oils selected from the group consisting of polybutene, hydrogenated polyisobutene, polyisoprene, polydecenes, and a mixture thereof; and
   v. one or more silicates;
      wherein the bleach composition is essentially anhydrous comprising less than 3 wt. % of water, based on the total weight of the bleach composition, and
      wherein the bleach composition forms a transparent ready-to-use hair bleaching composition having a pH above 7 and a refractory index of about 1.3 to about 1.4 at 25° C. when combined with a developer composition in a weight ratio of about 1:5 to about 5:1,
      wherein the developer composition comprises:
         i. about 2 to about 20 wt. %, based on the total weight of the developer composition, of hydrogen peroxide;
         ii. about 0.1 to about 20 wt. %, based on the total weight of the developer composition, of disteareth-100 IPDI; and
         iii. about 60 to about 96 wt. %, based on the total weight of the developer composition, of water.

6. A method for lightening the color of hair comprising:
   (a) applying a transparent ready-to-use hair bleaching composition of claim 1 to the hair;
   (b) leaving the composition on the hair for a period of time; and
   (c) rinsing the composition from the hair.

7. The bleach composition of claim 5, wherein the one or more acrylic polymers are chosen from sodium polyacrylate, carbomer, acrylates C10-30 alkyl acrylate crosspolymer, and a mixture thereof.

8. A transparent ready-to-use hair bleaching composition of claim 1 having a pH of 9 and above.

9. A transparent ready-to-use hair bleaching composition of claim 8 comprising about 25 to about 75 wt. % of water, based on the total weight of the transparent ready-to-use hair bleaching composition.

10. The kit of claim 4, wherein the bleach composition of (a) and the developer composition of (b) form a transparent ready-to-use hair bleaching composition having a pH of 9 and above when combined in a weight ratio of about 1:5 to about 5:1.

11. The bleach composition of claim 5, wherein the bleach composition forms a transparent ready-to-use hair bleaching composition having a pH of 9 and above when combined with the developer composition in a weight ratio of about 1:5 to about 5:1.

* * * * *